United States Patent [19]

Fishlock-Lomax

[11] Patent Number: 4,769,169
[45] Date of Patent: Sep. 6, 1988

[54] AMPHOTERIC SURFACTANTS FOR USE IN ANTIMICROBIAL CLEANING COMPOSITIONS

[75] Inventor: Eric G. Fishlock-Lomax, Chipping Warden, England

[73] Assignee: Amphoterics International Limited, England

[21] Appl. No.: 905,541

[22] Filed: Sep. 10, 1986

[30] Foreign Application Priority Data

Sep. 10, 1985 [GB] United Kingdom ............... 8522413

[51] Int. Cl.$^4$ .................. A61K 7/50; C11D 1/88
[52] U.S. Cl. ............... 252/106; 252/174.19; 252/527; 252/546
[58] Field of Search .......................... 252/106

[56] References Cited

U.S. PATENT DOCUMENTS 4,061,602  12/1977  Oberstar et al. ............ 252/547
4,292,212  9/1981  Melby ......................... 252/547

Primary Examiner—A. Lionel Clingman
Attorney, Agent, or Firm—Bacon & Thomas

[57] ABSTRACT

An amphoteric surfactant of formula (I)

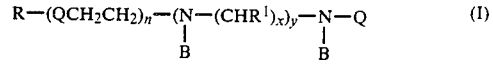

where R is a $C_{8-20}$ hydrocarbyl group, optionally substituted by hydroxyl or carboxyl;
$R^1$ is H or $C_{1-6}$ alkyl;
B is H or a group Q as defined below, B being a group Q in the majority of instances;
Q is $-R^2COOM$ where $R^2$ is $C_{1-6}$ alkylene and M is —H or an alkali metal, alkaline earth metal, ammonium or substituted ammonium ion;
x is 2 or 3;
y is 2 to 4; and
n is 0 or 1.

for use as an antimicrobial agent is cleaning compositions.

5 Claims, No Drawings

AMPHOTERIC SURFACTANTS FOR USE IN ANTIMICROBIAL CLEANING COMPOSITIONS

This invention relates to a group of amphoteric surfactants which have been found to possess antimicrobial properties and are useful in cleaning compositions for a wide range of applications including shampoos, laundry detergents and hard surface cleaners.

The invention concerns in particular a group of amphoteric surfactants which have been found to possess anti-microbial activity, e.g. against bacteria and fungi. They may therefore be included in anti-microbial cleaning compositions for topical application or general cleaning uses, for example anti-dandruff shampoos, skin cleansers and disinfecting cleaning compositions. The bactericidal properties are also useful in preserving shampoos or liquid detergents against bacterial growth and in conferring bactericidal properties to detergent compositions such as laundry detergents and hard surface cleaners. These surfactants also provide good conditioning action on the hair and are highly compatible with anionic shampoo ingredients. Practical tests have shown that said amphoterics do not build up on the hair and confer softness and excellent compatability. Said products are found to be non-irritant to the eyes (Draize test) and non-irritant and non-sensitising to the skin (Magnusson-Kligman test).

Another feature of this invention is the ability of said amphoterics to provide synergistic detergency, for example with non-ionic surfactants, and excellent solubilising and hydrotropic properties which are useful for example in stabilising mixtures of compositions. Such solubilising action allows the omission of separate hydrotropes, such as sodium xylene sulphonate, from such built detergents with considerable cost savings.

Amphoteric surfactants having antimicrobial properties in accordance with the invention have the general formula (I)

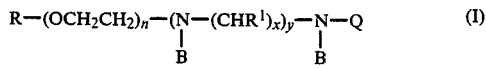

where R is a $C_{8-20}$ (e.g. $C_{12-18}$ or $C_{16-18}$) hydrocarbyl group, optionally substituted (e.g. by hydroxyl or carboxyl);
$R^1$ is H or $C_{1-6}$ alkyl;
B is H or a group Q as defined below, B being a group Q in the majority of instances;
Q is $-R^2COOM$ where $R^2$ is $C_{1-6}$ alkylene and M is $-H$ or an alkali metal, alkaline earth metal, ammonium or substituted ammonium ion;
x is 2 or 3;
y is 2 to 4; and
n is 0 or 1.

The invention thus provides antimicrobial compounds of formula (I) for use for example in cleaning or disinfecting or other microbicidal applications in relation to the human or animal body or inanimate objects or materials. The invention also includes compositions containing one or more of such compounds together with one or more inert carriers or diluents or other functional additives for use in such applications, particularly compositions such as shampoos for use in the treatment of dandruff which comprise one or more compounds of formula (I). The invention is also concerned with compositions of this type (especially shampoos, hard surface cleaners and laundry detergents) in which the compound(s) of formula (I) is or are the only or principal antimicrobial or preservative ingredient or in which other such ingredients are substantially absent.

Also included in the invention are cleaning methods comprising applying a microbicidally effective amount of one or more compounds of formula (I) to a human or animal body or an inanimate object or material for a period of time sufficient for the antimicrobial activity to be effective. In the treatment of dandruff in particular, a shampoo containing one or more surfactants of formula (I) may be used, preferably by repeated application to the head.

In the compounds of formula (I), R may for example be a straight or branched alkyl or alkenyl group; a cycloalkyl-alkyl (e.g. cyclohexyl-alkyl) group; an aralkyl or aralkenyl group in which the alkyl or alkenyl portion contains at least 6 carbon atoms; or the hydrocarbyl portion of a resinic acid containing at least two fused rings, e.g. as in the tricyclic pine resin acids such as abietic acid. However R is preferably a hydrocarbyl group derived from coco, tallow or oleic fatty acid.

In most surfactants of the formula (I) type, n is 0. Also, y is preferably 3 or 4. $R^1$ is preferably a hydrogen atom, but may be an alkyl group such as methyl.

In the group Q, $R^2$ may be an alkylene group such as methylene or ethylene and M is hydrogen or an alkali metal, alkaline earth metal, ammonium or substituted ammonium ion (e.g. mono-, di- or tri-hydroxyethylammonium). M is preferably sodium, and $R^2$ is preferably methylene.

Particularly preferred compounds of formula (I) have the formula (II)

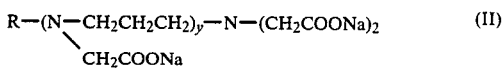

where R is as defined above (particularly a group derived from oleic or tallow fatty acid) and y is 3 or 4.

The invention also includes one or more compounds of formula (II) in which y is 3 in admixture with one or more compounds of formula (II) in which y is 4.

Surfactants of formula (I), particularly those of formula (II), have shown microbicidal (fungicidal and bactericidal) activity in tests against a number of organisms (in particular *E. Coli, Ps. aeruginosa, S. aureus* and *Pityrosporum ovale*), giving minimum inhibitory concentrations which are low (e.g. in the range of 0.015–0.06%) in comparison with the concentrations used in cleaning compositions. They have also been successful in long term tests against Penicillin sp., again showing minimum inhibitory concentrations well below in-use levels. The activity shown against *Pityrosporum ovale* is indicative of value in the treatment of dandruff and tests on volunteers using shampoos containing a surfactant of formula (II) have demonstrated that these compositions can be used effectively in the treatment of dandruff by repeated application.

In shampoo applications these amphoterics can be incorporated at levels of 0.01% to 25 or 50% (e.g. up to 15%) and preferably between 1% and 10% to confer excellent conditioning properties and useful antimicrobial properties (all percentages herein are by weight; amphoteric surfactants are normally supplied on a 30% active basis relative to undiluted material).

The shampoos preferably also contain an anionic surfactant (e.g. 5–50, preferably 5–25%), which may be any kind suitable for use in shampoos. Examples of suitable materials are sodium $C_{9-15}$ alkyl sulphates or ether sulphates (containing for example 1-4 moles ethylene oxide/mole) and the corresponding ammonium, mono-, di- and tri-ethanolamine salts. The anionic surfactant is preferably sodium lauryl sulphate or a sodium lauryl ether sulphate containing 1-4 (preferably 2 or 3) moles of ethylene oxide or a corresponding mono-, di- or tri-ethanolamine salt. (Anionic surfactants of this type are normally supplied on a 27-30% active basis).

Other surfactants (again, generally 5-50%, preferably 5-25%) may be incorporated such as coco dimethyl betaine, coco amidopropyl betaine, coco diethanolamide etc. For mild and frequent use shampoos coco amphoglycinate or coco amphocarboxyglycinate are normally used in conjunction with anionic surfactants such as those listed above. In all cases the amphoterics of this invention may be incorporated in partial replacement of or in addition to conventional shampoo surfactants.

The shampoos of the invention are water-based and if desired may contain additional ingredients such as normally included in shampoos, for example foam boosters (such as lauric diethanolamide or amine oxide), oils (e.g. jojoba or lemon), dyes and fragrances.

The invention also includes compositions for cleaning a wide range of items including hard surfaces and soft goods such as textiles both for commercial and home use. Examples of such compositions are liquid water-based cleaning compositions such as liquid detergents, carpet cleaners, dishwashing liquids and hard surface cleaners, but the same principles are equally applicable to solid compositions for example in powder form.

The surfactant of formula (I) is generally present in amounts of up to 25% in these cleaning compositions. Such compositions will usually include in addition to amphoteric surfactant of formula (I), one or more non-ionic surfactants or, if desired, one or more amphoteric surfactants of a different formula.

Depending on the intended use, the compositions may also contain additives conventionally included in cleaning formulations. For example other surfactant may be added for specific properties, for example to boost foam or to confer softening properties. Other additives may include alkaline builders to improve detergency, chelating or sequestering agents to avoid problems with heavy metal ions, optical brightening agents, solvents, dyes and perfumes.

Commercially available examples of the second amphoteric surfactant (having a different formula as compared to formula (I) above) which may be optionally included include products classed as cocoamphoglycinate or cocoamphopropionate (and similar products made from the other fatty acids), or cocamphocarboxyglycinate or cocoamphocarboxypropionate (and similar products made from the other fatty acids), for example Miranol CM, C2M or C2MSF.

In general the relative (weight) concentrations of the two amphoteric surfactants used is from 90:10 to 10:90, preferably 3:1 to 2:1 (first amphoteric:second amphoteric).

The non-ionic surfactants used are preferably ethylene oxide or propylene oxide/ethylene oxide adducts of alkylphenols (e.g. nonylphenol) or long chain alcohols or alkylamines (e.g. $C_{12-14}$ alcohols or $C_{12-18}$ alkylamines). The weight ratio of the principal amphoteric surfactant(s) to the non-ionic surfactant(s) is generally from 10:1 to 1:2, preferably from 2.5:1 to 1.5:1 (e.g. about 2:1).

The non-ionic surfactant may for example be a nonylphenol-ethylene oxide adduct containing 6-12 moles ethylene oxide, a $C_{12-14}$ alcohol-ethylene oxide adduct containing 7-10 moles ethylene oxide, a $C_{12-18}$ alkylamine-ethylene oxide adduct containing 7-15 moles ethylene oxide or an equivalent ethylene oxide/propylene oxide block copolymer adduct.

When a second non-ionic surfactant is included, it is may be of the same general type but is preferably more lipophilic than the main non-ionic surfactant. The second material may for example be a nonylphenolethylene oxide adduct containing 4-6 moles ethylene oxide, a $C_{12-14}$ alcohol-ethylene oxide adduct containing 4-6 moles ethylene oxide, a $C_{12-18}$ alkylamineethylene oxide adduct containing 2-5 moles ethylene oxide or an equivalent ethylene oxide/propylene oxide block copolymer adduct. A second non-ionic surfactant of this kind is generally used at a lower concentration than the first; for example, the weight ratio of the first to second surfactants may generally be from 100:1 to 60:40 or 70:30 in compositions containing a builder.

One of the advantages of the invention is that the choice of non-ionic surfactant is not as critical as in conventional detergent systems, for example as regards the balance of detergent properties and water solubility required particularly in built systems. The amphoteric surfactants also solubilise the non-ionic surfactants in formulations containing a builder.

The compositions may also contain, depending on the intended use, additives such as builders (e.g. sodium metasilicate (anhydrous or pentahydrate), tetrapotassium pyrophosphate, caustic soda or nitrilotriacetic acid), chelating or sequestering agents (e.g. trisodium nitrilotriacetic acid, tetrasodium ethylenediamine tetracetic acid and trisodium hydroxyethylethylenediamine triacetic acid), solvents (e.g. glycolethers such as butyl glycol ether, butyl cellosolve), fabric conditioners (e.g. quaternary ammonium salts, such as a di-fatty (usually tallow) dimethylammonium chloride (e.g. Arquad 2 HT) or a di-fatty (usually tallow) imidazoline methosulphate or ethosulphate quaternary salt (e.g. Ammonyx 4080 (Millmaster-Onyx), Imisoft 75 (M & S Chemicals) & Ampholak TQ (Amphoterics International)), foam boosters (such as alkyl betaines or amine oxides, e.g. Emigen BB & BT, Aromox DMDC (Akzo) and Empigen OB (Albright & Wilson), Ammonyx LO and CDO (Millmaster-Onyx), optical brighteners (e.g. Tinopal CBS-X & Tinopal 5BMS-X (Ciba)), dyes and perfumes.

The quantity of such additives used will vary according to the application and the nature of the particular additive. In general however liquid systems may contain 1-40% of a builder, 1-20% chelating agent, 1-10% solvent, 1-5% fabric conditioner, 1-5% foam booster, 0.1-1% optical brightener and 0.1-1% dyes and/or perfumes (percentages herein are by weight unless otherwise stated).

Liquid compositions which do not contain a builder may for example contain up to 50% of the principal amphoteric surfactant(s) and up to 25% non-ionic surfactants, e.g. up to 40% first (formula (I)) amphoteric surfactant, up to 10% second amphoteric surfactant (not of formula (I)), up to 20% first non-ionic surfactant and up to 5% second non-ionic surfactant.

Hard surface cleaners of the invention may for example have the following composition:

| | General | Preferred |
|---|---|---|
| Amphoteric (formula I) | 2-8% | 3-5% |
| 2nd Amphoteric | 1-4% | 1.5-2.5% |
| Non-ionic surfactant(s) | 1-6% | 2-4% |
| Solvent | 1-5% | 2-4% |
| Builder | 0-15% | 8-12% |
| Foam booster | 1-5% | 2-4% |
| Water to 100% | | |

The following examples illustrate the invention.

The amphoteric surfactant of formula (II) used in the following examples was Ampholak 7TX, available from Amphoterics International Limited, Leamington Spa, England. Ampholak 7TX/C may alternatively be used.

EXAMPLE 1

A shampoo was formulated to contain 10% active sodium lauryl ether sulphate and 5% of said amphoteric of preferred structure (formula II). The resulting shampoo was milder to the skin, offered conditioning effects and a degree of selfpreservation against microbiological attack.

EXAMPLE 2

A shampoo was formulated to contain 5% active sodium lauryl ether sulphate and 5% cocoamidopropyl betaine together with 2% of an amphoteric of formula (II). Beneficial results were similar to those obtained in Example 1.

EXAMPLE 3

A shampoo was formulated to contain 5% active sodium lauryl ether sulphate and 4% active coco amphocarboxyglycinate together with 1% active of the amphoteric of formula (II). A very mild shampoo was obtained, suitable for use as a baby shampoo or for a frequent use conditioning shampoo with beneficial results as above.

In the above examples active matter refers to 100% active basis and the pH was neutralised in each case to about 6.5 to 6.7 with citric acid solution.

Built liquid detergents are usually limited in the amount of surfactant and builder which can be combined together to yield a stable product. Even then it is usually necessary to add a solubiliser or hydrotrope which can account for a substantial proportion of the cost of the formulation. Use of the materials of formula (I) as shown in the following example allowed this hydrotrope to be completely omitted with significant cost saving and with the benefit of added bactericidal action.

EXAMPLE 4

The following formulations were prepared:

| | Conventional Formula | Improved Formula |
|---|---|---|
| TKPP* | 12% | 12% |
| Sodium Carbonate | 2% | 2% |
| Formula (II) Amphoteric | 0% | 2% |
| Anionic Surfactant | 2% | 0% |
| Nonionic Surfactant | 2% | 1% |
| Hydrotrope | 6% | 0% |
| Balance Water | | |

*tetrapotassium pyrophosphate

The improved formula showed better detergency at lower cost and also exhibited bactericidal properties.

Remarkable improvements have been found using the amphoterics of formula (I) in laundry washing detergents especially at lower temperatures such as 30° C. At lower temperatures it is desirable to incorporate a bactericide and the formula (I) amphoteric can be used to replace conventional bactericides in such systems.

EXAMPLE 5

A liquid laundry detergent was formulated as follows:

| Conventional Amphoteric (30% active) | 18% |
|---|---|
| Nonyl Phenol 9 E.O | 9% |
| Sodium Metasilicate Pentahydrate | 10% |
| Chelating Agent | 4% |
| Optical Brightening Agent | 0.2% |
| Balance Water | |

Improved detergency at 30° C. was obtained by replacing at least half of the above mentioned amphoteric with a formula (II) amphoteric, in addition to which valuable bactericidal properties were added.

I claim:

1. A method of anti-microbial cleaning which comprises applying to a body or object to be cleaned a microbicidally effective amount of an amphoteric surfactant of formula (I)

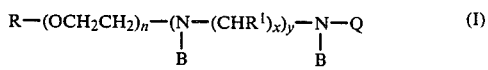

where
R is a $C_{8-20}$ hydrocarbyl group, optionally substituted by hydroxyl or carboxyl;
$R^1$ is H or $C_{1-6}$ alkyl;
B is H or a group Q as defined below, B being a group Q in the majority of instances;
Q is $-R^2COOM$, where $R^2$ is $C_{1-6}$ alkylene and M is —H or an alkali metal, alkaline earth metal, ammonium or substituted ammonium ion;
x is 2 or 3;
y is 2 to 4; and
n is 0 or 1.

2. A method according to claim 1 wherein the amphoteric surfactant has a formula (II)

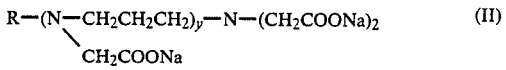

where y is 3 or 4.

3. A method according to claim 1 wherein the group R of the surfactant is a hydrocarbyl group derived from oleic or tallow fatty acids.

4. A method according to claim 1 comprising applying a microbicidally effective amount of said surfactant to the human head in the treatment of dandruff.

5. A method according to claim 2, wherein the surfactant comprises a surfactant of formula (II):

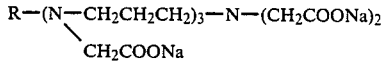

and at least one surfactant having the formula (II):

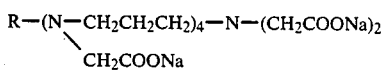

* * * * *

UNITED STATES PATENT AND TRADEMARK OFFICE
CERTIFICATE OF CORRECTION

PATENT NO. : 4,769,169

DATED : September 6, 1988

INVENTOR(S) : Eric G. Fishlock-Lomax

It is certified that error appears in the above-identified patent and that said Letters Patent is hereby corrected as shown below:

IN THE ABSTRACT:

In formula (I), please delete "$(QCH_2CH_2)_n$" and insert --$(OCH_2CH_2)_n$--.

Signed and Sealed this

Twenty-eighth Day of March, 1989

Attest:

DONALD J. QUIGG

*Attesting Officer*  *Commissioner of Patents and Trademarks*